US010966748B2

(12) United States Patent
Saleh

(10) Patent No.: US 10,966,748 B2
(45) Date of Patent: Apr. 6, 2021

(54) ENDOSCOPIC SNARE

(71) Applicant: Rafic Saleh, Aquadilla, PR (US)

(72) Inventor: Rafic Saleh, Aquadilla, PR (US)

( * ) Notice: Subject to any disclaimer, the term of this patent is extended or adjusted under 35 U.S.C. 154(b) by 165 days.

(21) Appl. No.: 16/202,080

(22) Filed: Nov. 27, 2018

(65) Prior Publication Data

US 2019/0159798 A1 May 30, 2019

Related U.S. Application Data

(60) Provisional application No. 62/591,114, filed on Nov. 27, 2017.

(51) Int. Cl.
*A61B 17/3205* (2006.01)
*A61B 17/221* (2006.01)
*A61B 18/14* (2006.01)
*A61B 18/00* (2006.01)

(52) U.S. Cl.
CPC ...... *A61B 17/32056* (2013.01); *A61B 17/221* (2013.01); *A61B 18/1492* (2013.01); *A61B 2017/2212* (2013.01); *A61B 2018/00267* (2013.01); *A61B 2018/141* (2013.01)

(58) Field of Classification Search
CPC ............ A61B 17/32056; A61B 17/221; A61B 18/1492; A61B 17/2212; A61B 2018/00267; A61B 17/320725; A61B 17/225; A61B 2018/141
See application file for complete search history.

(56) References Cited

U.S. PATENT DOCUMENTS

| 3,791,387 A | 2/1974 | Itoh |
| 4,625,726 A | 12/1986 | Duthoy |
| 5,190,542 A | 3/1993 | Nakao et al. |
| 5,201,740 A | 4/1993 | Nakao et al. |
| 5,345,936 A | 9/1994 | Pomeranz et al. |
| 5,486,182 A | 1/1996 | Nakao et al. |
| 5,643,263 A | 7/1997 | Younker |
| 5,713,853 A | 2/1998 | Clark et al. |

(Continued)

FOREIGN PATENT DOCUMENTS

CA 2261111 C 6/2005

OTHER PUBLICATIONS

PCT International Search Report—PCT/US18/62679—dated Mar. 8, 2019.

(Continued)

*Primary Examiner* — Katrina M Stransky
(74) *Attorney, Agent, or Firm* — James R. Young; Cochran Freund & Young LLC

(57) ABSTRACT

An endoscopic snare device (10, 100, 100') includes a pair of bowed, resiliently deformable, snare wires (12, 14) with bow shaped memory, a mesh (20) attached to mid-portions (16, 18) and distal portions (22, 24) of the snare wires (12, 14) for a mesh length (A) that is less than the snare length (L), a bowed, resiliently deformable, support wire (116) extending in a plane out of the plane of the snare wires (12, 14), and a pair of bowed, resiliently deformable, incising wires (112, 114) side by side with the snare wires (12, 14). The support wire (116) is electrically insulated. A mouth cord or wire (46) extends from one snare wire (12), through the support wire (116), and to the other snare wire (14).

16 Claims, 7 Drawing Sheets

(56) References Cited

U.S. PATENT DOCUMENTS

| | | |
|---|---|---|
| 5,720,754 A | 2/1998 | Middleman et al. |
| 5,741,271 A | 4/1998 | Nakao et al. |
| 5,846,248 A | 12/1998 | Chu et al. |
| 5,997,547 A | 12/1999 | Nakao et al. |
| 6,077,274 A | 6/2000 | Ouchi et al. |
| 6,183,482 B1 | 2/2001 | Bates et al. |
| 6,217,589 B1 | 4/2001 | McAlister |
| 6,224,612 B1 | 5/2001 | Bates et al. |
| 6,235,026 B1 | 5/2001 | Smith |
| 6,267,776 B1 | 7/2001 | O'Connell |
| 6,277,138 B1 | 8/2001 | Levinson et al. |
| 6,348,056 B1 | 2/2002 | Bates et al. |
| 6,458,145 B1 | 10/2002 | Ravenscroft et al. |
| 6,500,182 B2 | 12/2002 | Foster |
| 6,585,734 B2 | 7/2003 | Levinson |
| 6,656,191 B2 | 12/2003 | Ouchi |
| 6,673,080 B2 | 1/2004 | Reynolds et al. |
| 6,743,237 B2 * | 6/2004 | Dhindsa ............ A61B 17/221 606/127 |
| 6,814,729 B2 | 11/2004 | Secrest et al. |
| 6,883,000 B1 | 4/2005 | Gropper |
| 7,270,663 B2 | 9/2007 | Nakao |
| 7,326,220 B1 | 2/2008 | Goldstein |
| 7,678,119 B2 | 3/2010 | Little et al. |
| 7,914,540 B2 | 3/2011 | Schwartz et al. |
| 2002/0042617 A1 | 4/2002 | Ouchi |
| 2003/0109889 A1 | 6/2003 | Mercereau |
| 2003/0176888 A1 | 9/2003 | O'Connell |
| 2004/0059345 A1 | 3/2004 | Nakao |
| 2004/0199048 A1 | 10/2004 | Clayman et al. |
| 2004/0199202 A1 | 10/2004 | Dubrul et al. |
| 2005/0119668 A1 | 6/2005 | Teague |
| 2005/0267489 A1 | 12/2005 | Secrest |
| 2006/0100641 A1 | 5/2006 | Teague |
| 2006/0129166 A1 | 6/2006 | Lavelle |
| 2007/0016224 A1 | 1/2007 | Nakao |
| 2007/0255289 A1 | 11/2007 | Nakao |
| 2008/0091215 A1 | 4/2008 | Saleh |
| 2008/0306336 A1 | 12/2008 | Kaye et al. |
| 2012/0165815 A1 | 6/2012 | Collins et al. |
| 2013/0023895 A1 | 1/2013 | Saleh |

OTHER PUBLICATIONS

Supplementary Partial European Search Report, EP 12 81 8329, dated Feb. 12, 2015 (dated Feb. 12, 2015), 6 pages.
International Search Report, PCT/US20121045671, dated Oct. 1, 2012 (dated Oct. 1, 2012), 12 pages.

* cited by examiner

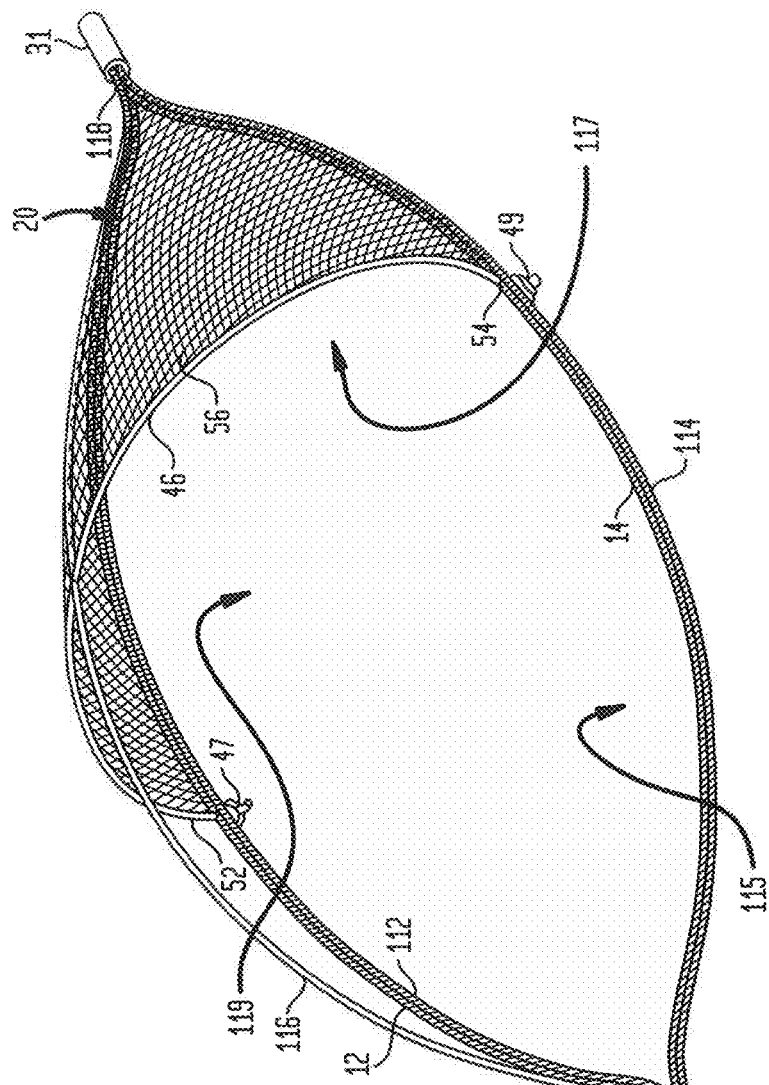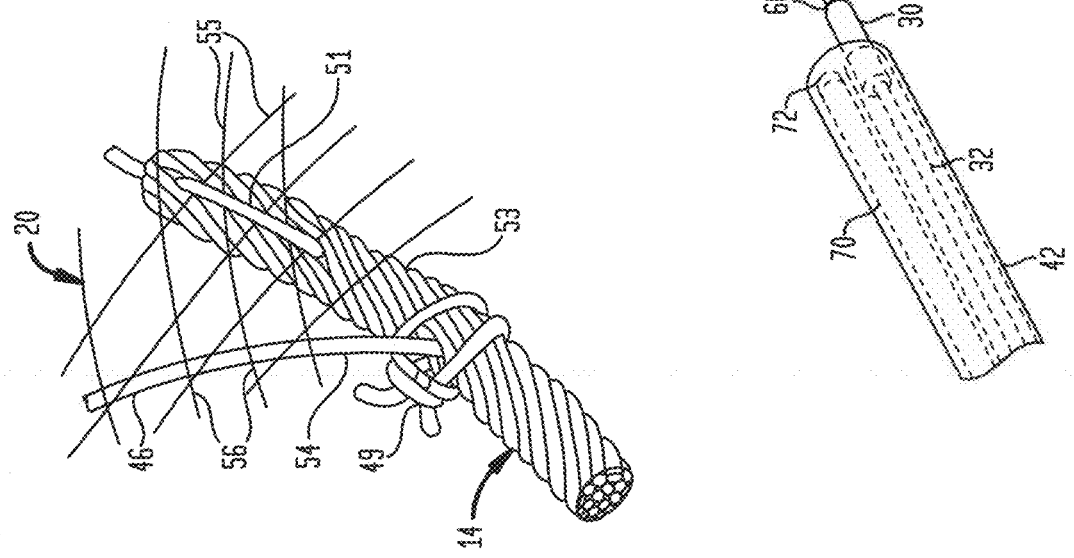

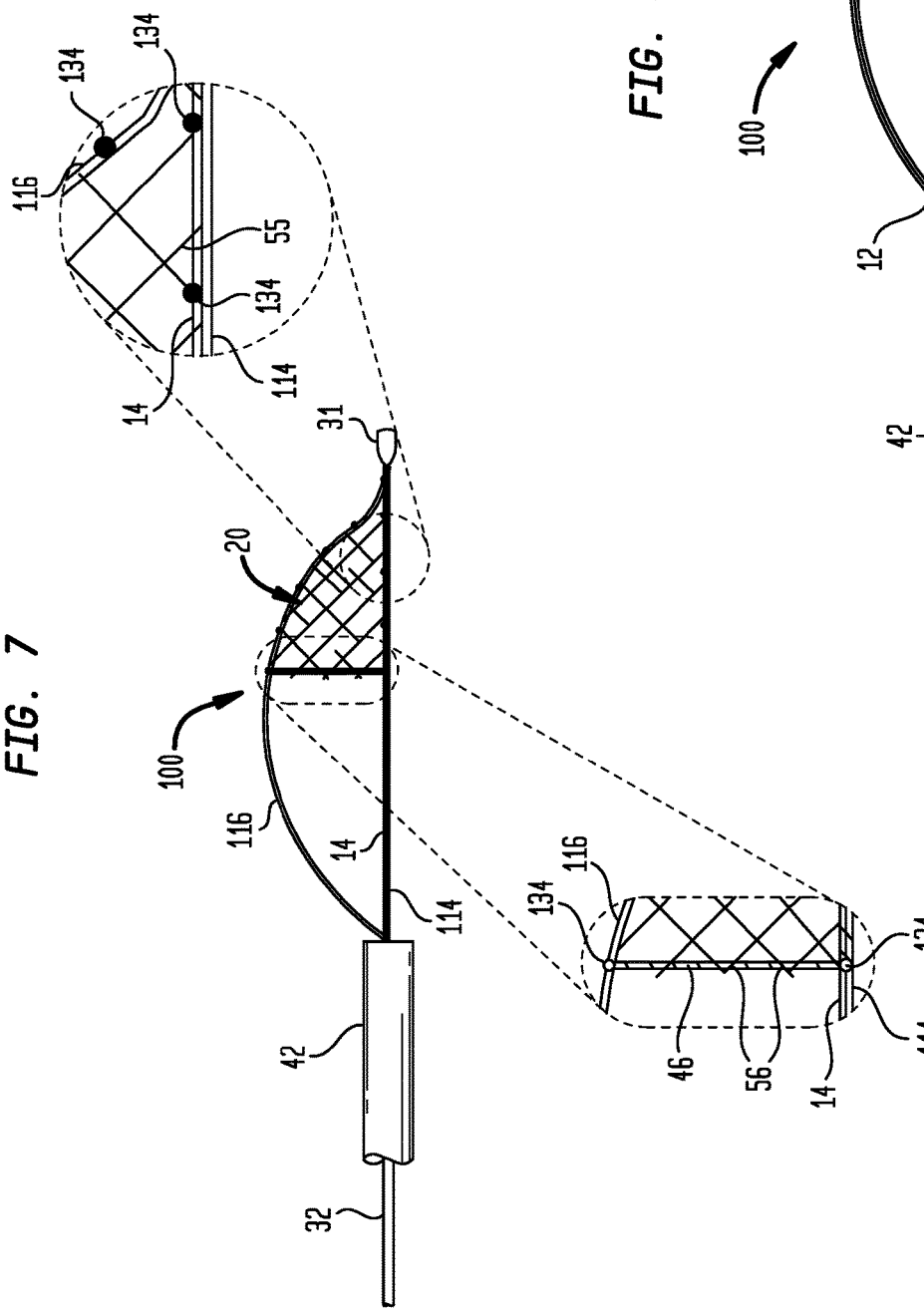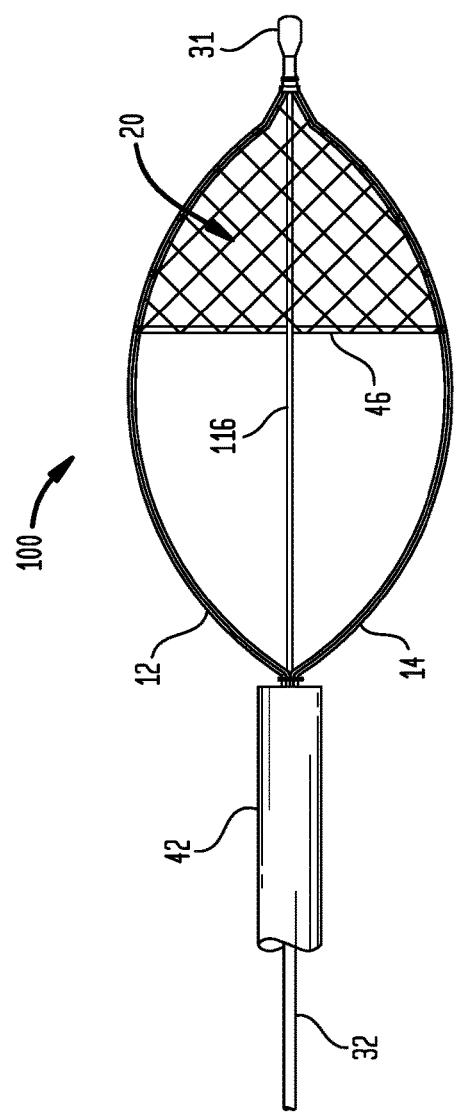

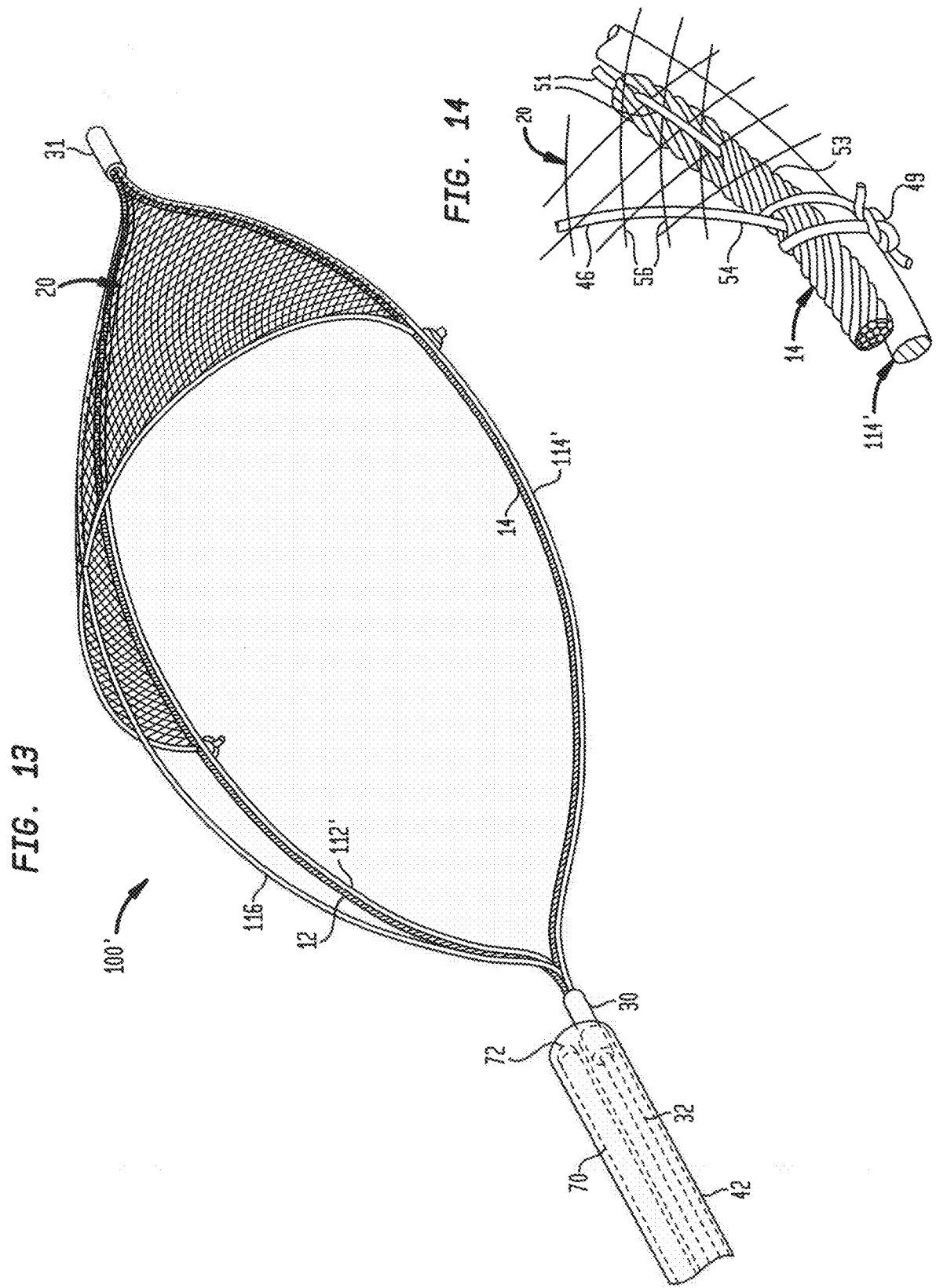

ENDOSCOPIC SNARE

BACKGROUND

Field of the Invention

This invention is related to endoscopic surgical devices for capturing and removing tissue pieces from insides of organs or body cavities accessed endoscopically, including, for example, polyps from colons.

Background

Endoscopic tools or tips for endoscopically finding, incising, capturing, and removing or retrieving tissue, such as polyps and many others, from inside human organs are myriad and well-known. Ideally, each incised targeted tissue is captured quickly and removed from the person's body, especially if the targeted tissue is to be biopsied for disease (for example biopsying incised polyps for cancer). However, many incising tools and retrieval tools are separate, so the tissue is first incised with one tool and captured and retrieved with another tool. After incising tissues, surgeons often cannot see where incised tissues (e.g., polyps) are located and spend a lot of time looking for them. Sometimes, the incised tissues are lost and never found, which means they are never biopsied, and, if diseased, such disease is not discovered. Therefore, such lost and not recovered tissues could have serious consequences. For example, if a cancerous polyp that is lost and not biopsied, the cancer may not be discovered, and, by the time the person has another colonoscopy years later, the cancer could have spread and become advanced stage colon cancer.

The foregoing examples of the related art and limitations related therewith are intended to be illustrative and not exclusive.

BRIEF DESCRIPTION OF THE DRAWINGS

The accompanying drawings, which are incorporated herein and form a part of the specification, illustrate some, but not the only or exclusive, example embodiments or features. It is intended that the embodiments and figures disclosed herein are to be considered illustrative rather than limiting.

FIG. 5 is an enlarged view of the attachment of the mouth cord or wire and the mesh to the snare wire of the example snare in FIG. 1;

FIG. 6 is an isometric view of a second example snare;

FIG. 7 is an enlarged side elevation view of the second example snare of FIG. 6;

FIG. 8 is an enlarged top plan view of the second example snare of FIG. 6;

FIG. 13 is an isometric view of another example snare; and

FIG. 14 is an enlarged perspective view of the attachment of the mouth cord or wire and the mesh to the snare wire of the example snare of FIG. 13.

DETAILED DESCRIPTION OF EXAMPLE EMBODIMENTS

Figure 1:
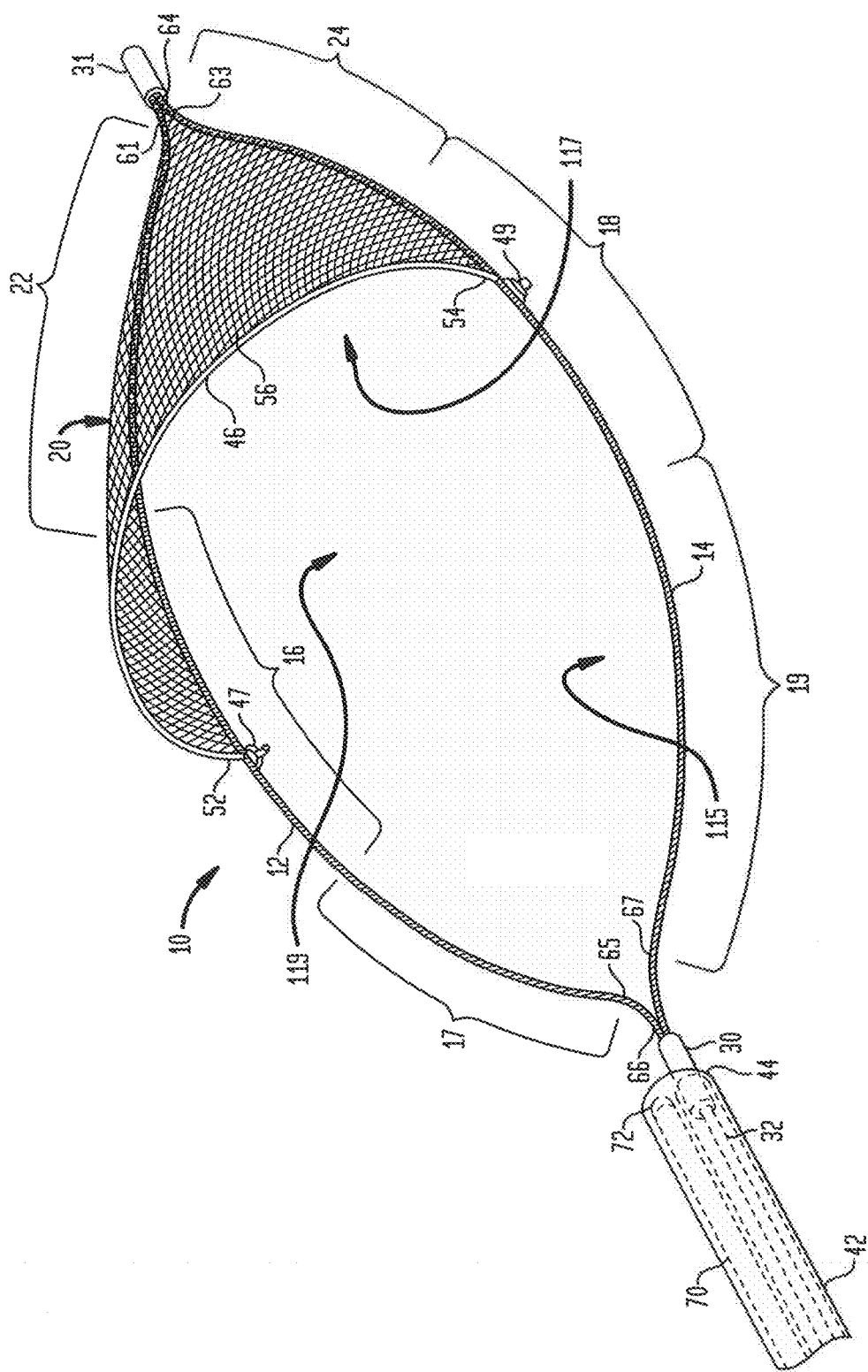
FIG. 1 is an isometric view of a first example snare.
Figure 2:
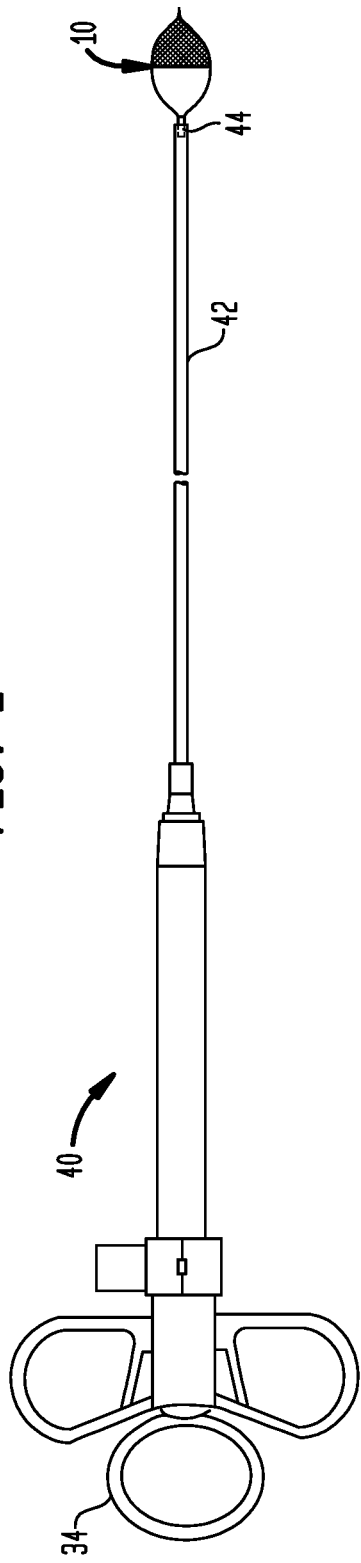
FIG. 2 is a side elevation view of the example snare of FIG. 1 mounted on a distal end of an example endoscopic instrument with which the example snare in FIG. 1 can be implemented.
Figure 4:
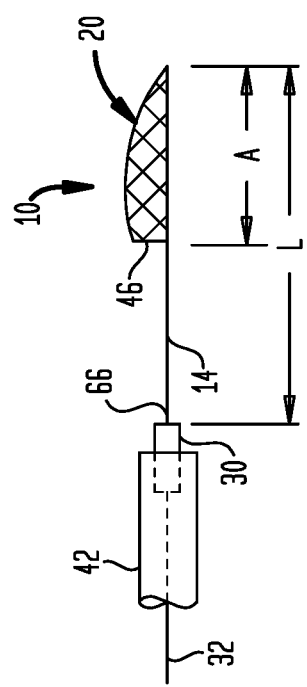
FIG. 4 is an enlarged side elevation view of the example snare in FIG. 1 mounted on the distal end of the example endoscopic instrument of FIG. 2.
Figure 3:
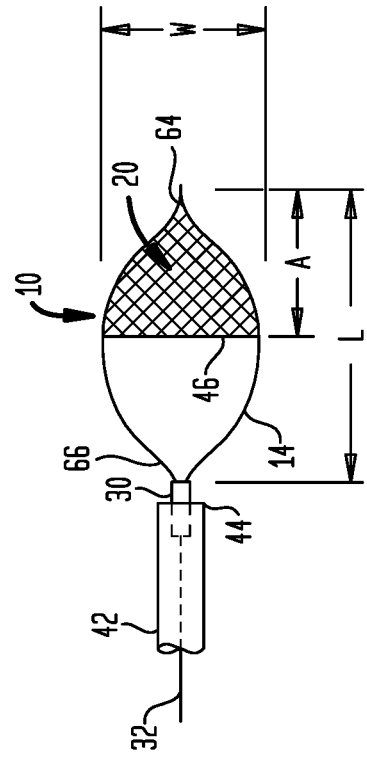
FIG. 3 is an enlarged top plan view of the example snare of FIG. 1 mounted on the distal end of the example endoscopic instrument of FIG. 2.

An example rotatable snare 10 for use in endoscopically snaring, incising, capturing, and removing tissue pieces and other materials from organs or body cavities (not shown) is illustrated in FIGS. 1-5. The example snare 10 in those figures comprises a pair of snare wires 12, 14 that have a resilient bias to separate their mid-portions 16, 18 a width W away from each other, which defines a snare wire plane 115 that extends through the snare wires 12, 14. A mesh 20 is attached to the respective snare wires 12, 14, including mid-portions 16, 18 and distal portions 22, 24 of the snare wires 12, 14, but not to proximal portions 17, 19. The snare wires 12, 14 are attached together at their proximal ends, for example, by a ferrule 30 to a control wire 32. As best seen in FIG. 1, the pair of snare wires 12, 14 and the mesh 20 together form a basket with an interior space 117 over the snare wire plane 115 and with an unobstructed opening 119 in the snare wire plane 115 to the interior space and no obstruction below the opening 119. As also shown in FIGS. 1, 3, and 4, the proximal marginal edge portion 56 of the mesh 20 forms the mouth of the basket. As illustrated in FIG. 2, the control wire 32 extends from a control mechanism 34 of an endoscopic instrument 40, through the tubing 42 (also sometimes called cannula or catheter) of the endoscopic instrument 34 to the ferrule 30 at or near the distal end 44 of the tubing 42. A mouth cord 46 (or wire) may be provided to strengthen or support the proximal end 56 (mouth end) of the mesh 20, which functions as a basket to catch pieces of tissue that are incised by the snare wires 12, 14, or as a scoop to capture loose pieces of tissue as will be explained in more detail below. If such a cord or wire 46 is provided at the mouth end 56 of the basket formed by the mesh 20, such mouth cord or wire 46 can be attached at each end 52, 54 to opposite respective mid-portions 16, 18 of the snare wires 12, 14 in any convenient manner that is secure and does not slip, for example, by extending the ends 52, 54 through strands 53 of the snare wires 12, 14 and tying knots 47, 49 as illustrated in FIG. 5, or, as another example, through eyelets in the snare wires as shown in U.S. Pat. No. 9,101,342 B2 issued to Rafic Saleh on Aug. 11, 2015, all of which is incorporated herein by reference for all that it describes (see, for example, eyelets 64 in U.S. Pat. No. 9,101,342 B2 FIGS. 17 and 18). The mesh 20 can be attached to the snare wires 12, 14, for example, with laces 51 laced through the lateral marginal edge portions 55 of the mesh 20 and through strands 53 of the snare wires 12, 14, as also illustrated FIG. 5, or, for example, in a manner similar to any of the attachments of surround materials to snare wires in U.S. Pat. No. 9,101,342 B2 (see, for example, the attachments of surround materials to the snare wires in U.S. Pat. No. 9,101,342 B2 FIGS. 21-26). Likewise, if the mouth cord or wire 46 is provided as shown in FIGS. 1-5, the proximal end 56 of the mesh 20 can be attached to the cord or wire 46, for example, by weaving the cord or wire 46 through the proximal marginal edge portion 56 of the mesh 20 as illustrated in FIG. 5, or, for example, in any manner similar to the attachments of surround materials to snare wires in U.S. Pat. No. 9,101,342 B2 with ties or laces threads around or through the cord or wire 46 and through the marginal edge portion of the mesh 20 at the proximal end 56 of the mesh 20.

Figure 9:
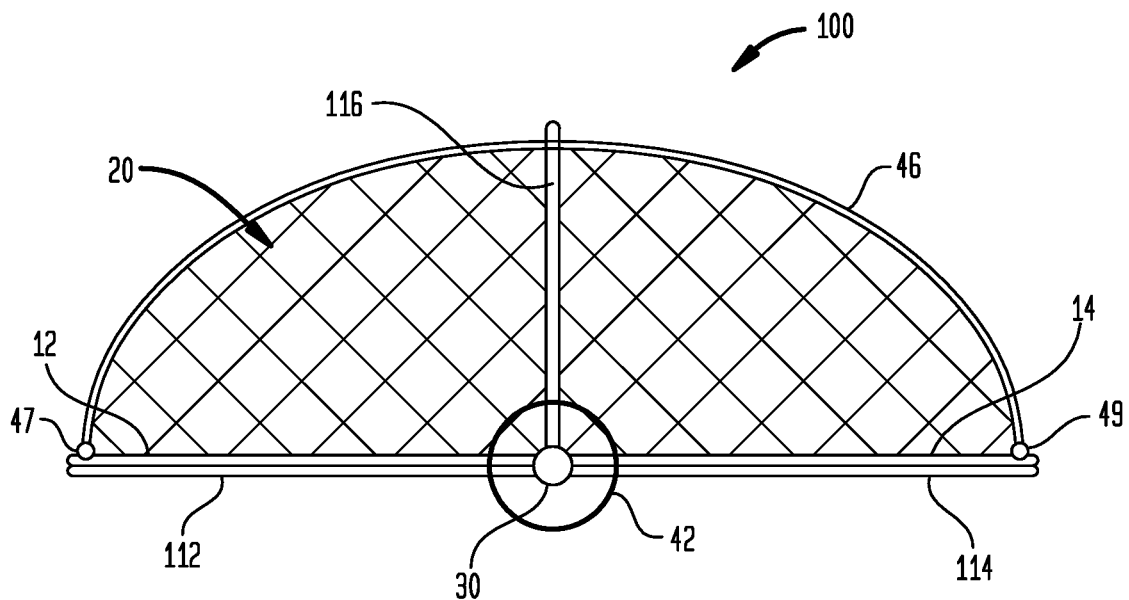
FIG. 9 is an enlarged proximal end view of the second example snare of FIG. 6.
Figure 10:
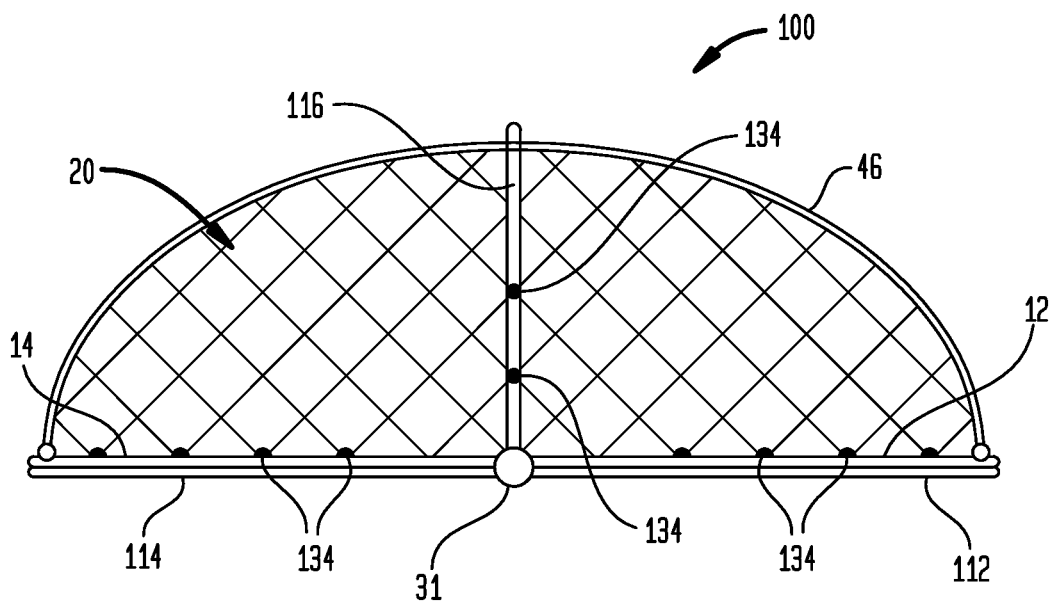
FIG. 10 is an enlarged distal end view of the second example snare of FIG. 6.

The snare 10 can be pulled by the control wire 32 into the cannula 42 and pushed by the control wire 32 out of the cannula 42 in a manner similar to the surgical retrieval apparatus described in U.S. Pat. No. 9,101,343 B2 (see, for example, U.S. Pat. No. 9,101,342 B2 FIGS. 9 and 10). As the snare 10 is pulled into the cannula 42, the distal end of the cannula 42 forces the snare wires 12, 14 together to collapse the snare 10. As the snare 10 is pushed out of the cannula 42, the resilient snare wires 12, 14 separate to from each other to the configuration illustrated in FIGS. 1-4 with a snare length L and snare width W.

The example snare 10 in FIGS. 1-5 is illustrative of the snare 10 with the mesh 20 wider than the distance between the two snare wires 12, 14 so that the mesh 20 forms a pocket or basket adjacent to the two snare wires 12, 14 for catching tissue that is incised from an organ (e.g., a polyp incised from a colon). The cord or wire 46 shown in FIGS. 1-5 is longer than the width W of the snare, and it can be bendable with some resiliency for holding the extended shape of the mouth or, if desired, it can be limp with little or no resiliency, The mesh 20 can have some stiffness for maintaining an extended shape, if desired, or it can be made of limp material, which allows the mesh 20 to hang loose and enhances the ability of the mesh 20 to surround and hold a tissue piece that is incised from an organ. With the cord or wire 46 longer than the width W of the snare 10 and resiliently semi-rigid or stiff so it can hold the mesh 20 open and somewhat outstretched, even when rotated and inverted, which enhances the use of the mesh 20 as a scoop to catch and retrieve loose tissue pieces, e.g., tissue pieces that may not have been caught by the mesh 20 when the tissue was initially incised by the snare wires 12, 14. The distal ends 61, 63 of the snare wires 12, 14 can be attached together at the distal end 64 of the snare 10 by a ferrule 31, as shown in FIG. 5, or by any other convenient device or method. The proximal ends 65, 67 of the snare wires 12, 14 can be attached together at the proximal end 66 of the snare 10 and to the control wire 32 by the ferrule 30 in a rigid manner so that rotation of the control wire 32 causes the snare 10 to also rotate. Accordingly, the control wire 32 can be rotatable in the cannula 42 by the control mechanism 34 to rotate the deployed snare 10 to any orientation as needed or desired by a surgeon using the endoscopic instrument 40 and snare 10.

As shown best seen in FIGS. 1 and 5, the snare wires 12, 14 in the example snare 10 are stranded wires with some resilience and memory to the extended shape illustrated in FIGS. 1-4, although solid wires could be used. The snare wires 12, 14, in the example snare 10 in FIGS. 1-5 can be either hot or cold for excising tissue. For example, the snare wires 12, 14 can be made with an ohmic material, such as an electrically conductive metal, and in a manner that can be heated by electrical resistance as is known in the art. For example, if a monopolar circuit is used, electricity can be applied to the control wire 32, which electrifies the snare wires 12, 14, and a return electrode can be provided in contact with the patient as is known in the art. If the snare wires 12, 14 are made to be hot, the mesh 20 and the mouth cord or wire 46 can be made of respective materials that can withstand the heat of the snare wires 12, 14.

It is common for endoscopic instruments, such as the endoscopic instrument 40 and tube or cannula 42, to be equipped with an optical lumen 70 and optical components 72 that enable the surgeon to see the deployed snare 10 and surrounding tissue through the distal end 44 of the cannula 42 as illustrated generally in FIG. 1. Essentially, the surgeon looks through such an optical lumen 70 in the cannula 42 for a targeted tissue (e.g., polyps in a person's colon), and, when such targeted tissue is found, the surgeon maneuvers the snare into position to incise the targeted tissue. If the snare used by the surgeon does not have anything to capture and retrieve the incised tissue, then a surgical retrieval basket, for example, a surgical retrieval basket as shown in U.S. Pat. No. 9,101,342 B2, is then used by the surgeon to capture and retrieve the incised targeted tissue for removal from the person's body. Ideally, each incised targeted tissue is captured quickly and removed from the person's body, especially if the targeted tissue is to be biopsied for disease (for example biopsying incised polyps for cancer). In practice, however, surgeons often cannot see where incised tissues (e.g., polyps) are located and spend a lot of time looking for them. Sometimes, the incised tissues are lost and never found, which means they are never biopsied, and, if diseased, such disease is not discovered. Therefore, such lost and not recovered tissues could have serious consequences. For example, if a cancerous polyp that is lost and not biopsied, the cancer may not be discovered, and, by the time the person has another colonoscopy years later, the cancer could have spread and become advanced stage colon cancer.

In contrast, excising of the targeted tissue with the snare 10 illustrated in FIGS. 1-5 occurs at the distal end 64 of the snare 10 and the mesh 20 captures and retains the incised tissue immediately before it can move away from the excision site. As mentioned above, the mesh 20 is attached to mid-portions 16, 18 and to distal portions 22, 24 of the respective snare wires 12, 14, so that targeted tissue incised by the distal end portions 22, 24 of the snare wires 12, 14 can be caught immediately by the mesh 20. The mesh 20 does not extend the full length L of the snare 10, i.e., of the snare wires 12, 14, from the distal end 64 to the proximal end 66 of the snare 10 so that the mesh 20 does not obstruct the surgeon's vision as the surgeon looks through the distal end 44 of the cannula 42 to a tissue being incised. As shown in FIGS. 1, 3, and 4, the length A of the mesh 20 is in a range of about one-fourth to three-fourths of the length L of the snare 10, depending on a surgeon's preference for better sight at the expense of slightly diminished mesh capture and holding capacity or better mesh capture and holding capacity at the expense of diminished vision. A mesh 20 length A of about one-half or slightly less than one-half of the length L of the snare 10 provides a suitable optimum of vision and holding capacity that may be satisfactory for many surgeons, but a variety of snares 10 with different mesh length A to snare length L ratios can be provided for different situations.

For some applications or to meet some surgeon's preferences, some additional structural support may be desired to hold the mesh 20 in open, extended shape. Accordingly, another example snare 100 is illustrated in FIGS. 6-14, which provides such additional support for the mesh 20 and for the mouth cord 46 to hold them open (extended) and to provide additional protection for the lateral marginal edge portions of the mesh 20 as tissue (e.g., a polyp or other tissue) is being incised. In FIGS. 6-14, components and features of the example snare 100 that are the same as components in the example snare 10 in FIGS. 1-5 are numbered the same, so it is not necessary to repeat descriptions of those components and features for an understanding of the example snare 100.

In the example snare 100, incising wires 112, 114, which are essentially duplicates of the snare wires 12, 14, respectively, are provided side by side with the snare wires 12, 14. The lateral marginal edge portions 55 of the mesh 20 are still attached to the snare wires 12, 14, as explained above, but the incising wires 112, 114 bear a significant portion of the contacts and forces that incise the tissue, thereby providing some shielding and protection against such contacts and forces on the lateral marginal edge portions 55 of the mesh 20 and on the laces 51 that attach the lateral marginal edge portions 55 of the mesh to the snare wires 12, 14 as described above. Also, a support wire 116 is provided to support the mouth cord or wire 46 and the mesh 20 in open, extended shape. As illustrated in FIGS. 6-10, the support wire 116 is arch-shaped in a support wire plane that is substantially perpendicular to a snare wire plane 115 that extends through the snare wires 12, 14, and the mesh 20 extends over (outside) of, or attached to, the support wire 116 so that the support wire 116 supports the mesh 20 in a direction extending away from the snare wire plane 115 that extends through the snare wires 12, 14, i.e., in an open, extended shape. The distal end 118 of the support wire 116 is connected rigidly with the distal ends of the snare wires 12, 14 by the distal ferrule 31, and the proximal end 120 of the support wire 116 is connected rigidly with the proximal ends of the snare wires 12, 14 by the proximal ferrule 30. Accordingly, as best seen in FIG. 6. the snare wires 12, 14, the support wire 116. and the mesh 20 together form a basket by partially enclosing an interior space 117 between the snare wire plane 115 and the support wire 116 with an unobstructed opening 119 in the snare wire plane 115 to the interior space 117 and no obstruction below the opening 119. The proximal edge portion 56 of the mesh 20 forms the mouth of the basket at the mesh length A, which is less than the snare length L, as explained above and shown in FIGS. 3 and 4. The support wire 116 bends and collapses like the snare wires 12, 14 when the control wire 32 pulls the snare 10 into the tube (cannula) 42, and it expands to its extended shape when the control wire 32 pushes the snare 10 out of the tube (cannula) 42.

Figure 11:
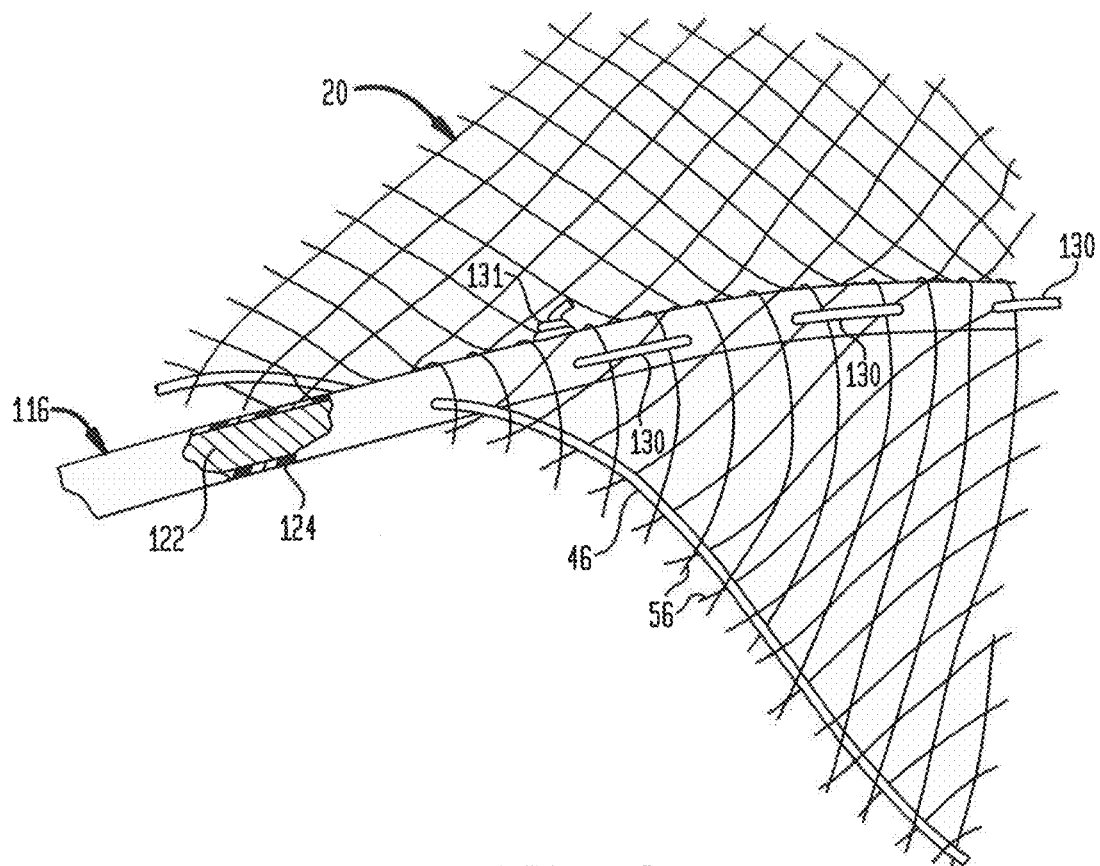
FIG. 11 is an enlarged perspective view of an example attachment of the mouth cord or wire and the mesh to the support wire of the example snare of FIG. 6.

The support wire 116 can be made of a resiliently bendable, stranded wire 122 like the snare wires 12, 14. However, if the snare wires 12, 14 and the incising wires 112, 114 are to be heated for hot excision of tissue, the support wire 116 is insulated with electrical insulation 124 as best seen in FIG. 11, so that the stranded wire 122 of the support wire 116 does not touch tissue, thus does not form part of the electrical circuit that heats the snare wires. Accordingly, the support wire 116 is not heated by the electric circuit and functions only to keep the mouth wire 46 and mesh 20 open and extended while the tissue is being incised by the incising wires 112, 114 and the snare wires 12, 14.

As also best seen in FIG. 11, the mouth cord or wire 46 can be poked (e.g., with a needle or awl) through the insulation 124 and stranded wire 122 for a secure, non-slip attachment of the mouth cord or wire 46 to the support wire 116. Similarly, laces 130 can be used to fasten the mesh 120 to the support wire 166. The end of the lace 130 can be tied in a knot 132 so that the lace 130 stays in place.

Figure 12:
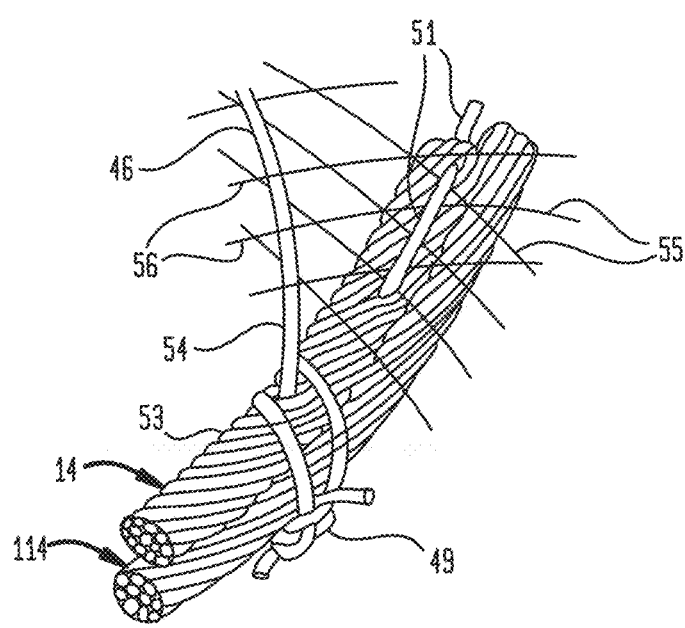
FIG. 12 is an enlarged perspective view of the attachment of the mouth cord or wire and the mesh to the snare wire of the example snare of FIG. 6.

The ends 52, 54 of the mouth cord or wire 46 can be poked through the stranded snare wires 12, 14, and tied in knots 47, 49 as explained above for the example snare 10, but, as best seen in FIG. 12, the ends 52, 54 (52 not seen in FIG. 12) can be tied around the snare wires 12, 14 and also around the incising wires 112, 114 to bind the incising wire 112 to the snare wire 12 and to bind the incising wire 114 to the snare wire 14 and their mid-portions to provide additional structural integrity to the snare 100, especially as the snare 100 is being pulled into the tube 42. However, as mentioned above, the laces 51 attach the mesh 20 to the snare wires 12, 14 in the example snare 100 as in the example snare 10, not to the incising wires 112, 114. Other attachments, for example, ties and knots 134, as illustrated diagrammatically in FIG. 7 could also be used for attaching the mesh 20 to the snare wires 12, 14 and to the support wire 116 as explained above and shown, for example, in the U.S. Pat. No. 9,101,342 B2.

Another example snare 100' shown in FIGS. 13 and 14 is substantially like the example 100 snare in FIGS. 6-12, except the incising wires 112' and 114' are solid instead of stranded.

The foregoing description provides examples that illustrate the principles of the invention, which is defined by the features that follow. Since numerous insignificant modifications and changes will readily occur to those skilled in the art once they understand the invention, it is not desired to limit the invention to the exact example constructions and processes shown and described above. Accordingly, resort may be made to all suitable combinations, subcombinations, modifications, and equivalents that fall within the scope of the invention as defined by the claims. The words "comprise," "comprises," "comprising," "include," "including," and "includes" when used in this specification, including the features, are intended to specify the presence of stated features, integers, components, or steps, but they do not preclude the presence or addition of one or more other features, integers, components, steps, or groups thereof. The terms upper, upwardly, lower, bottom, top, down, downwardly, vertical, horizontal, and other directional terms in this description are in reference to the diagrammatic orientations depicted in the drawings and are only used for convenience and clarity in this description unless otherwise indicated. They are not intended to limit the snares to any particular orientation in real use applications, and, in fact, the snares can be positioned, rotated, and used in any desired orientation.

The embodiments of the invention in which an exclusive property or privilege is claimed are defined as follows:

1. Endoscopic snare apparatus, comprising:
   a pair of bowed, resiliently deformable, snare wires with bow shaped memory fastened together at a proximal end, said snare wires extending longitudinally in radially flared relation to each other to a distal end at a snare length L from the proximal end;
   a mouth cord extending from a non-slip attachment to a mid-portion of one of the snare wires to a-non-slip attachment to the other one of the snare wires; and
   a mesh attached to mid-portions and distal portions of the snare wires for a mesh length A that is less than the snare length L, and wherein a proximal marginal edge portion of the mesh is attached to the mouth cord.

2. The endoscopic snare apparatus of claim 1, wherein the mesh length A is in a range of one-fourth to three-fourths of the snare length L.

3. The endoscopic snare apparatus of claim 1, wherein the pair of bowed, resiliently deformable, snare wires define a snare wire plane, and wherein the endoscopic snare apparatus includes a bowed, resiliently deformable, support wire that extends out of the snare wire plane.

4. The endoscopic snare apparatus of claim 3, wherein the support wire extends out of the snare wire plane in a support wire plane that is substantially perpendicular to the snare wire plane.

5. The endoscopic snare apparatus of claim 3, wherein the mouth cord is attached in a non-slip matter to the stranded support wire.

6. The endoscopic snare apparatus of claim 3, wherein the bowed, resiliently deformable, support wire is insulated electrically.

7. The endoscopic snare apparatus of claim 6, wherein the bowed, resiliently deformable, support wire is stranded and coated in electrical insulation.

8. The endoscopic snare apparatus of claim 7, wherein the mouth cord extends through the stranded support wire.

9. The endoscopic snare apparatus of claim 7, wherein the mesh extends over the support wire.

10. The endoscopic snare apparatus of claim 7, wherein the mesh is attached to the support wire.

11. Endoscopic snare apparatus, comprising:
   a pair of bowed, resiliently deformable, snare wires with bow shaped memory fastened together at a proximal end, said snare wires extending longitudinally in radially flared relation to each other to a distal end at a snare length L from the proximal end;
   a pair of bowed, resiliently deformable, incising wires with bow shaped memory fastened together positioned side by side with the pair of bowed, resiliently deformable, snare wires, respectively, said incising wires each having a distal end and a proximal end, wherein the distal ends of the incising wires are attached together with the distal ends of the snare wires and the proximal ends of the incising wires are attached together with the proximal ends of the snare wires; and
   a mesh attached to mid-portions and distal portions of the snare wires for a mesh length A that is less than the snare length L from the proximal end.

12. The endoscopic snare apparatus of claim 11, wherein mid-portions of the incising wires are attached to respective mid-portions of the snare wires.

13. The endoscopic snare apparatus of claim 11, wherein the pair of bowed, resiliently deformable, snare wires define a snare wire plane, and wherein the endoscopic snare apparatus includes a bowed, resiliently deformable, support wire that extends out of the snare wire plane.

14. The endoscopic snare apparatus of claim 3, wherein the support wire extends out of the snare wire plane in a support wire plane that is substantially perpendicular to the snare wire plane.

15. Endoscopic snare apparatus, comprising:
   a pair of bowed, resiliently deformable, snare wires with bow shaped memory fastened together at a proximal end, said snare wires extending longitudinally in radially flared relation to each other to a distal end at a snare length L from the proximal end in a manner that defines a snare wire plane between the pair of bowed snare wires, the pair of snare wires having resilient bias to separate mid-portions of the snare wires a width W away from each other; and
   a mesh attached in a non-slip manner to mid-portions and distal portions of the snare wires for a mesh length A that is less than the snare length L such that a proximal marginal edge portion of the mesh extends from a non-slip attachment to the mid-portion of one of the pair of snare wires to a non-slip attachment to the mid-portion of the other one of the pair of snare wires, the proximal marginal edge portion being longer than the width W between the mid-portions of the bowed snare wires, whereby the bowed snare wires and mesh together form a basket partially enclosing an interior space over the snare wire plane with an unobstructed opening in the snare wire plane between the snare wires to the interior space and no obstruction below the opening, and with the proximal marginal edge portion of the mesh forming a basket mouth over the snare wire plane.

16. Endoscopic snare apparatus, comprising:
   a pair of bowed, resiliently deformable, snare wires with bow shaped memory fastened together at a proximal end, said snare wires extending longitudinally in radially flared relation to each other to a distal end at a snare length L from the proximal end in a manner that defines a snare wire plane between the pair of bowed snare wires;
   a bowed, resiliently deformable, support wire that is fastened together with the snare wires at the proximal end and extends out of, and over, the snare wire plane and then converges together with the snare wires at the distal end; and
   a mesh attached to mid-portions and distal portions of the snare wires for a mesh length A that is less than the snare length L, and wherein the mesh extends from the snare wires over the snare wire plane and is fastened in a non-slip manner to the support wire; whereby the snare wires, support wire, and mesh together form a basket partially enclosing an interior space between the snare wire plane and the support wire with an unobstructed opening to the interior space in the snare wire plane between the snare wires and no obstruction below the opening, and with a proximal marginal edge portion of the mesh forming a basket mouth over the snare wire plane.

\* \* \* \* \*